United States Patent [19]

Fujimura et al.

[11] 4,278,672
[45] Jul. 14, 1981

[54] PHARMACEUTICAL COMPOSITION AND METHODS OF USE CONTAINING 1,1,3,5-SUBSTITUTED BIURET COMPOUND

[75] Inventors: Hajime Fujimura, Kyoto; Yasuzo Hiramatsu, Otsu; Takahiro Yabuuchi, Takarazuka; Masakatu Hisaki, Hikone; Katsuo Takikawa, Naruto; Takaji Honna, Tokushima; Hidekazu Miyake, Tokushima; Makoto Kajitani, Tokushima, all of Japan

[73] Assignee: Taiho Pharmaceutical Company, Limited, Tokyo, Japan

[21] Appl. No.: 134,555

[22] Filed: Mar. 27, 1980

[30] Foreign Application Priority Data

Mar. 31, 1979 [JP] Japan .................................. 54/38792
Mar. 31, 1979 [JP] Japan .................................. 54/38794

[51] Int. Cl.$^3$ .................... A61K 27/00; A61K 31/40; A61K 31/165; A61K 31/445
[52] U.S. Cl. ................. 424/248.4; 424/267; 424/274; 424/324
[58] Field of Search ............... 424/324, 274, 248.4, 424/267

[56] References Cited

U.S. PATENT DOCUMENTS

3,189,431 6/1965 Salzberg ................................. 71/2.6

FOREIGN PATENT DOCUMENTS

1096006 12/1967 United Kingdom .

OTHER PUBLICATIONS

J.A.C.S., 62 1595 (1940).

*Primary Examiner*—Stanley J. Friedman
*Attorney, Agent, or Firm*—Murray and Whisenhunt

[57] ABSTRACT

An analgesic, anti-inflammatory or anti-pyretic composition containing 1,1,3,5-substituted biuret compound of the formula,

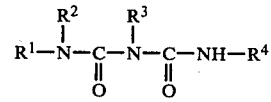

wherein $R^1$ is a lower alkyl group or a phenyl group; $R^2$ is a lower alkyl group, a phenyl group or a substituted phenyl group having chlorine atom(s), methyl group(s) or methoxy group(s) as the substituent(s), further $R^1$ and $R^2$ may form a single ring containing one or two hetero atoms including the adjacent nitrogen atom; $R^3$ is a hydrogen atom, a lower alkyl group or a phenyl group; $R^4$ is a phenyl group, a substituted phenyl group having halogen atom(s), trifluoromethyl group(s), methyl group(s), methoxy group(s), dimethylamino group(s), nitro group(s), hydroxyl group(s), acetyl group(s) or methylthio group(s) as the substituent(s), a benzyl group, a cyclohexyl group or a lower alkyl group, as the active ingredient.

6 Claims, No Drawings

PHARMACEUTICAL COMPOSITION AND METHODS OF USE CONTAINING 1,1,3,5-SUBSTITUTED BIURET COMPOUND

The present invention relates to a pharmaceutical composition containing a 1,1,3,5-substituted biuret compound. More particularly, the present invention relates to an analgesic, anti-inflammatory or anti-pyretic composition containing 1,1,3,5-substituted biuret compound of the formula (1),

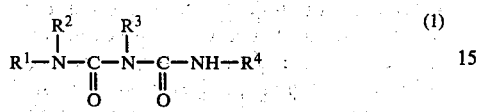

wherein $R^1$ is a lower alkyl group or a phenyl group; $R^2$ is a lower alkyl group, a phenyl group or a substituted phenyl group having chlorine atom(s), methyl group(s), or methoxy group(s) as the substituent(s), further $R^1$ and $R^2$ may form a single ring containing one or two hetero atoms including the adjacent nitrogen atom; $R^3$ is a hydrogen atom, a lower alkyl group or a phenyl group; $R^4$ is a phenyl group, a substituted phenyl group having halogen atom(s), trifluoromethyl group(s), methyl group(s), methoxy group(s), dimethylamino group(s), nitro group(s), hydroxyl group(s), acetyl group(s) or methylthio group(s) as the substituent(s), a benzyl group, a cyclohexyl group or a lower alkyl group, as the active ingredient.

Hitherto, some of 1,1,3,5-substituted biuret compounds represented by the formula (1) are known. On the other hand, although the definitions of the substituents in the formula (1) are different, other substituted biuret compounds having the basic structure of the formula,

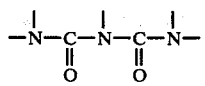

which is common to the formula (1) are known.

There have been reported that some of such known substituted biuret compounds, especially the latter compounds having the above-mentioned basic structure, have hypotensive, sedative or anti-convulsive activity. However, the prior art has not been aware that either 1,1,3,5-substituted biuret compounds represented by the general formula (1) or other biuret compounds, having the above-mentioned basic structure which is common to the general formula (1), have analgesic, anti-inflammatory or anti-pyretic activity. [cf. British Pat. No. 1,096,006; U.S. Pat. No. 3,189,431 and J. Amer. Chem. Soc., 62, 1595 (1940)].

The present invention is base on the facts that the 1,1,3,5-substituted biuret compounds represented by the general formula have analgesic, anti-inflammatory or anti-pyretic activity.

The object of the present invention is to provide novel 1,1,3,5-substituted biuret compounds.

Another object of the present invention is to provide an analgesic, anti-inflammatory or anti-pyretic composition containing 1,1,3,5-substituted biuret compound as the active ingredient.

Among the 1,1,3,5-substituted biuret compounds of the formula (1), the following compounds are novel ones.

1,1-Dimethyl-5-(2-fluorophenyl)biuret
1,1-Dimethyl-5-(4-methoxyphenyl)biuret
1,1,3-Trimethyl-5-phenylbiuret
1,1,3-Trimethyl-5-(2-fluorophenyl)biuret
1,1,3-Trimethyl-5-(4-fluorophenyl)biuret
1,1,3-Trimethyl-5-(2,3,5,6-tetrafluorophenyl)biuret
1,1,3-Trimethyl-5-(2-chlorophenyl)biuret
1,1,3-Trimethyl-5-(3-chlorophenyl)biuret
1,1,3-Trimethyl-5-(4-chlorophenyl)biuret
1,1,3-Trimethyl-5-(2,4-dichlorophenyl)biuret
1,1,3-Trimethyl-5-(3,4-dichlorophenyl)biuret
1,1,3-Trimethyl-5-(2,6-dichlorophenyl)biuret
1,1,3-Trimethyl-5-(4-bromophenyl)biuret
1,1,3-Trimethyl-5-(2-trifluoromethylphenyl)biuret
1,1,3-Trimethyl-5-(3-trifluoromethylphenyl)biuret
1,1,3-Trimethyl-5-(4-dimethylaminophenyl)biuret
1,1,3-Trimethyl-5-(4-nitrophenyl)biuret
1,1,3-Trimethyl-5-(4-hydroxyphenyl)biuret
1,1,3-Trimethyl-5-(2-methoxyphenyl)biuret
1,1,3-Trimethyl-5-(4-methoxyphenyl)biuret
1,1,3-Trimethyl-5-(3,4-dimethoxyphenyl)biuret
1,1,3-Trimethyl-5-(3,4,5-trimethoxyphenyl)biuret
1,1,3-Trimethyl-5-(2-methylphenyl)biuret
1,1,3-Trimethyl-5-(3-methylphenyl)biuret
1,1,3-Trimethyl-5-(4-methylphenyl)biuret
1,1,3-Trimethyl-5-(2,3-dimethylphenyl)biuret
1,1,3-Trimethyl-5-(3,4-dimethylphenyl)biuret
1,1,3-Trimethyl-5-(2,6-dimethylphenyl)biuret
1,1,3-Trimethyl-5-(2-methyl-3-chlorophenyl)biuret
1,1,3-Trimethyl-5-(4-acetylphenyl)biuret
1,1,3-Trimethyl-5-(4-methylthiophenyl)biuret
1,1,3-Trimethyl-5-cyclohexylbiuret
1,1-Dimethyl-3-ethyl-5-phenylbiuret
1,1-Dimethyl-3-n-propyl-5-phenylbiuret
1,1-Dimethyl-3-n-butyl-5-phenylbiuret
1,1,5-Trimethyl-3-phenylbiuret
1,1-Dimethyl-3-phenyl-5-n-propylbiuret
1,1-Dimethyl-3-phenyl-5-cyclohexylbiuret
1-Methyl-1-ethyl-5-phenylbiuret
1-Methyl-1-ethyl-5-benzylbiuret
1,3-Dimethyl-1-ethyl-5-phenylbiuret
1,3-Dimethyl-1-n-propyl-5-phenylbiuret
1-Methyl-1-n-butyl-5-phenylbiuret
1,3-Dimethyl-1-n-butyl-5-phenylbiuret
1,5-Dimethyl-1-phenylbiuret
1-Methyl-1-phenyl-5-ethylbiuret
1-Methyl-1-phenyl-5-n-propylbiuret
1-Methyl-1-phenyl-5-n-butylbiuret
1,3-Dimethyl-1-phenyl-5-ethylbiuret
1,3-Dimethyl-1-phenyl-5-n-propylbiuret
1,3-Dimethyl-1-phenyl-5-isopropylbiuret
1,1-Diethyl-3-methyl-5-phenylbiuret
1Ethyl-1-phenyl-3,5-dimethylbiuret
1-Ethyl-1-(2-chlorophenyl)-3,5-dimethylbiuret
1-Ethyl-1-(4-chlorophenyl)-3,5-dimethylbiuret
1-Ethyl-1-(4-methoxyphenyl)-3,5-dimethylbiuret
1-Ethyl-1-(4-methylphenyl)-3,5-dimethylbiuret
1-n-Propyl-1-phenyl-3,5-dimethylbiuret
1-n-Butyl-1-phenyl-3,5-dimethylbiuret
1,1-Diphenyl-3,5-dimethylbiuret
1,1-Ethylene-3-methyl-5-phenylbiuret
1,1-Tetramethylene-5-phenylbiuret
1,1-Tetramethylene-3-methyl-5-phenylbiuret
1,1-Pentamethylene-5-phenylbiuret
1,1-Pentamethylene-3-methyl-5-phenylbiuret 1,1-(3-Oxapentamethylene)-5-phenylbiuret
1,1-(3-Oxapentamethylene)-3,5-dimethylbiuret
1,1-(3-Oxapentamethylene)-3-methyl-5-phenylbiuret The 1,1,3,5-substituted biuret compound of the formula (1) can be prepared by any processes shown below.

REACTION PROCESS-A

Reaction of an urea compound of the formula (2) with an isocyanate of the formula (3) to obtain the 1,1,3,5-substituted biuret compound of the formula (1) as follows:

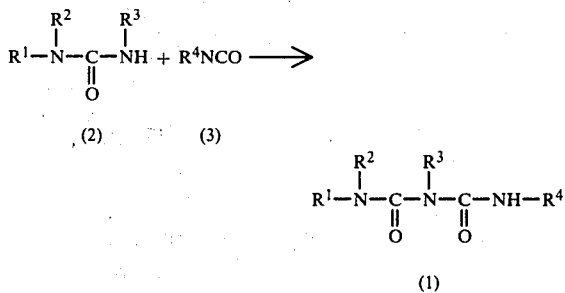

This reaction process-A is actually classified to the following three methods.

REACTION PROCESS-A-1

The reaction of the urea compound (2) with the isocyanate compound of (3) is carried out in the absence or presence of a solvent. The solvent used in this reaction is not subjected to any specific restriction and any known inert type which gives no adverse effect to the reaction can be used. Among the examples of the solvents are ethers such as ether, dioxane, tetrahydrofuran and the like; halogenated lower alkanes such as methylene chloride, chloroform, carbon tetrachloride and the like; aromatic hydrocarbons such as benzene, toluene, xylene and the like. The ratio of amount of the urea compound (2) and the isocyanate compound (3) in this reaction is not subjected to any specific restriction and may be suitably selected from a wide range, and usually, it is desirable that they are used in equimolar quantity respectively. The reaction temperature is also not subjected to any particular restriction and may be suitably selected from a wide range, and usually the reaction can advantageously be carried out at a room temperature to the boiling point of the solvent used. The thus obtained 1,1,3,5-substituted biuret compound (1) can be isolated by usual separation means.

REACTION PROCESS-A-2

The reaction of the urea compound (2) with the isocyanate (3) is carried out in the presence of a catalyst in a solvent. As to the catalyst, basic catalysts such as sodium hydride, sodium amide and the like can be used. The solvent is not subject to any specific restriction and any known type which gives no adverse effect to the reaction can be used. Among the examples of the solvents, ethers such as ether, dioxane, tetrahydrofuran and the like; aromatic hydrocarbons such as benzene, toluene, xylene and the like can be used. The ratio of amount of the urea compound (2) and the isocyanate compound (3) may be selected from a wide range, and usually it is desirable that they are used in equimolar quantity respectively. The amount of catalyst may also be selected from a wide range. The reaction temperature may also be selected from a wide range, and usually the reaction can advantageously be carried out at from $-20°$ C. to a room temperature. The thus formed 1,1,3,5-substituted biuret compound (1) can be isolated by usual separation means.

REACTION PROCESS-A-3

The reaction of the urea compound (2) with the isocyanate compound (3) is carried out in the presence of a Lewis acid in a solvent. At to the Lewis acid, anhydrous aluminum chloride, anhydrous stannic chloride, titanium tetrachloride and the like can be used. The solvent is not subjected to any specific restriction and any known inert type which gives no adverse effect to the reaction can be used. Among the examples of the solvents, halogenated lower alkanes such as chloroform, methylene chloride, carbon tetrachloride and the like; aromatic hydrocarbons such as benzene, toluene, xylene and the like can be used. The ratio of amounts of the urea compound (2), the isocyanate compound (3) and the Lewis acid may be selected from a wide range, and usually, it is desirable that they are used in equimolar quantity respectively. The reaction temperature may also be selected from a wide range, and usually the reaction can advantageously be carried out at $-20°$ C. to a room temperature. The 1,1,3,5-substituted biuret compound (1) is formed as a complex with the Lewis acid, and a free form thereof can easily be obtained by treating the complex with a diluted mineral acid such as a diluted hydrochloric acid or a diluted sulfuric acid at a room temperature under stirring condition.

REACTION PROCESS-B

Reaction of an allophanoyl chloride of the formula (4) with an amine of the formula (5) to obtain the 1,1,3,5-substituted biuret compound of the formula (1) is shown as follows:

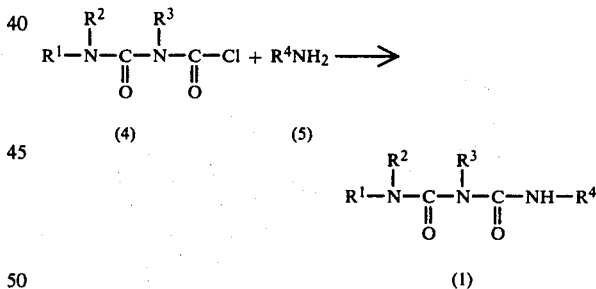

The reaction may usually be carried out in a solvent. The solvent is not subjected to any specific restriction and any known inert type which gives no adverse effect to the reaction can be used. Among the examples of the solvents, halogenated lower alkanes such as methylene chloride, chloroform, carbon tetrachloride and the like; aromatic hydrocarbons such as benzene, toluene, xylene and the like may be used. If necessary, basic compounds such as trialkylamines, pyridine bases and the like may be used as suitable condensation agent. The ratio of amounts of the allophanoyl chloride (4) and the amine (5) may suitably be selected from a wide range, and usually, it is desirable that the amine (5) is used in equimolar to 2 times the molar quantity of the allophanoyl chloride (4). The reaction temperature may also be selected from a wide range, and the reaction can advantageously be carried out in the range of from $-20°$ to +50° C. Thus formed 1,1,3,5-substituted buiret compound (1) can easily be isolated by usual separation means.

REACTION PROCESS C

Reaction of a 1,3-diazetidine-2,4-dione of the formula (6) with an amine of the formula (7) to obtain 1,1,3,5-substituted biuret compound of the formula (1) is shown as follows:

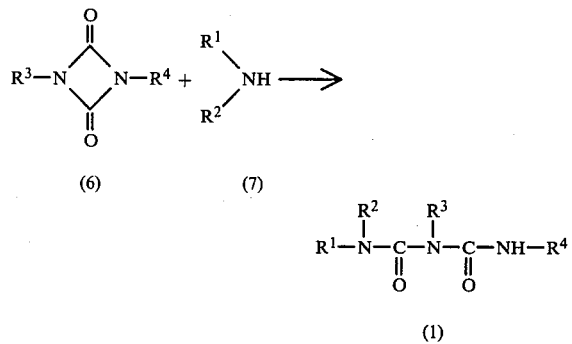

This reaction may usually be carried out in a solvent. The solvent used in this reaction is not subjected to any specific restriction and any known inert type which gives no adverse effect to the reaction can be used. Generally, water, aceton, acetonitrile and the like may be used as the solvent. The ratio of amounts of the 1,3-diazetidine-2,4-dione (6) and the amine (7) in this reaction is not subjected to any specific restriction and may be suitably selected from a wide range, and usually, it is desirable that the amine (7) is used in equimolar to 2 times the molar quantity of the 1,3-diazetidine-2,4-dione (6). The reaction temperature is also not subjected to any particular restriction, and the reaction can advantageously be carried out at a room temperature to about 100° C. The thus formed 1,1,3,5-substituted buiret compound of the formula (1) can be isolated by usual separation means.

Most of the 1,1,3,5-substituted buiret compounds of the formula (1) of the present invention [that is, all compounds, except those of formula (1') below] have analgesic, anti-inflammatory and anti-pyretic activities. However, among of those compounds, 1,1,3,5-substituted biuret compounds of the formula (1'),

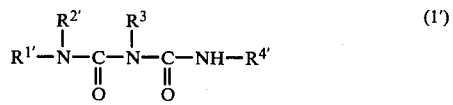

wherein $R^{1'}$ is a lower alkyl group; $R^{2'}$ is a lower alkyl group, a phenyl group, a substituted phenyl group having chlorine atom(s) or methoxy group(s) as the substituent(s); further $R^{1'}$ and $R^{2'}$ may form a single ring containing one or two heterto atoms including the adjacent nitrogen atom; $R^3$ is a hydrogen atom, a lower alkyl group or a phenyl group; $R^{4'}$ is a phenyl group, a substituted phenyl group having halogen atom(s), trifluoromethyl group(s), methyl group(s), methoxy group(s), dimethylamino group(s), nitro group(s) or acetyl group(s) as the substituent(s), a benzyl group, a cyclohexyl group or a lower alkyl group, have only anti-inflammatory activity.

The 1,1,3,5-substituted buiret compound of the formula (1) of the present invention can be administered in the range of from 10 to 2,000 mg per day, preferably from 50 to 1,000 mg per day, for an adult, as an analgesic, anti-inflammatory or anti-pyretic agent. The administration of the compound is carried out by dividing the above-mentioned daily dosage into 2 or 3 portions. Said dosage of the compound may be adjusted in consideration of the clinical conditions and age of the patient.

The administration may be carried out in the form of peroral preparations, injection preparations, suppository preparations for rectal use, topical preparations and the like.

An analgesic, anti-inflammatory or anti-pyretic composition containing the present 1,1,3,5-substituted biuret compound of the formula (1) is prepared and administered by formulating with conventional pharmaceutically acceptable carriers or excipients through a common method.

Peroral preparations such as tablets, capsules, granules, powders, etc. may contain excipients used generally in the art. Said excipients are exemplified such as calcium carbonate, calcium phasphates, starch, sucrose, lactose, talc, magnesium stearate, gelatine, polyvinylpyrrolidone, gum arabic, sarbitol, microcrystalline cellulose, polyethyleneglycol, carboxymethylcellulose, silica, polyvinylacetal diethylaminoacetate, hydroxypropyl methylcellulose, shellac, etc. Further, the tablets may be coated with a suitable coating by a common method known in the arts. Peroral liquid form preparations may be of aqueous or oily suspensions, syrups, elixiers and the like and are prepared by common methods. Injection preparations may be of aqueous or oily suspensions, powdery or lyophilyzed preparations which is dissolved upon use. These preparations may be prepared by a common method.

The present substituted biuret compound may be administered as a suppository composition for rectal use, which may be contain pharmaceutically acceptable carriers, known in the art, such as polyethylene glycols, lanoline, cacao butter, fatty acid triglycerides and the like.

As to preparations for topical use, the substituted biuret compound of the formula (1) of the present invention may be administered in the form of an ointment or cream which is prepared by formulating with a suitable ointment base and other additives by common method.

EXAMPLES OF THE INVENTION

The present invention is further explained in detail by illustrating examples of synthesis of the substituted buiret compounds in Table 1; and pharmacological tests including analgesicc activity test, anti-inflammatory activity test and anti-pyretic activity test in Table 2 together with examples of pharmaceutical preparations.

EXAMPLE 1

Synthesis of 1-ethyl-1-methyl-5-phenylbiuret (Compound No. 43 in Table 1) by reaction process A-1

In 50 ml of anhydrous dioxane, 7.7 g (0.075 mole) of 1-ethyl-1-methyl-urea was dissolved, into this solution 8.9 g (0.075 mole) of phenylisocyanate was added dropwise under stirring condition. The reaction was continued at a room temperature for 15 hours, then the precipitate thus formed was obtained by filtration and recrystallized from ethanol to obtain 10.8 g (yield 65%) of 1-ethyl-1-methyl-5-phenylbuiret having a melting point of 157°–159° C.

EXAMPLE 2

Synthesis of 1-ethyl-1,3-dimethyl-5-phenylbiuret (Compound No. 45 in Table 1) by reaction process A-2

In 300 ml of anhydrous tetrahydrofuran, 2.9 g (0.06 mole) of sodium hydride (50% in oil) was added thereto. The mixture was cooled below 10° C. and 7.0 g (0.06 mole) of 1-ethyl-1,3-dimethylurea was added to the mixture under stirring. The reaction was then continued at a room temperature for 15 hours. Next the reaction mixture was cooled below 0° C. and 7.1 g (0.06 mole) of phenyl isocyanate was added dropwise with stirring. The reaction was continued at about 0° C. for 3 hours, then the solvent was removed by distillation under reduced pressure to obtain a residue. Ice-water was added to the residue and 1 N-hydrochloric acid was added to make the mixture acidic, then extracted with chloroform. The extracted liquor was dried with anhydrous sodium sulfate and the solvent was removed by distillation under reduced pressure to obtain a residue. The residue was recrystallized from ethanol-petroleum ether to obtain 7.2 g (yield, 51%) of 1-ethyl-1,3-dimethyl-5-phenylbiuret having a melting point of 88.5°–90.5° C.

EXAMPLE 3

Synthesis of 1,5-dimethyl-1-phenylbiuret (Compound No. 49 in Table 1) by reaction process A-3

In 150 ml of anhydrous dichloromethane, 7.0 g (0.05 mole) of 1-methyl-1-phenylurea was dissolved and under cooling with ice-water, with stirring, 2.9 g (0.05 mole) of methyl isocyanate was poured thereinto and further 13.0 g (0.05 mole) of stannic chloride was added dropwise. The reaction was continued at a room temperature for 15 hours to form precipitates. The precipitates were obtained by filtration and 30 ml of 20% hydrochloric acid—60 ml of chloroform was added and stirred. The reaction was continued until the reaction mixture become transparent, then the chloroform layer was separated, and washed with water. The chloroform layer was dried wih anhydrous sodium sulfate and the solvent was removed by distillation under a reduced pressure to obtain a residue. The residue was recrystallized from ether-petroleum ether to obtain 8.3 g (yield 80%) of 1,5-dimethyl-1-phenylbiuret having a melting point of 123°–125° C.

EXAMPLE 4

Synthesis of 1,1-diethyl-3-methyl-5-phenylbiuret (Compound No. 57 in Table 1) by reaction process A-3

In 300 ml of anhydrous dichloromethane, 13.0 g (0.1 mole) of 1,1-diethyl-3-methylurea and 12.0 g (0.1 mole) of phenylisocyanate were dissolved. Under cooling the mixture with stirring, 26.0 g (0.1 mole) of stannic chloride was added dropwise. The reaction was continued at a room temperature for 15 hours and the reaction mixture was treated by a procedure similar to that of mentioned in Example 1, and recrystallized from ethanol-petroleum ether to obtain 19.7 g (yield 79%) of 1,1-diethyl-3-methyl-5-phenylbiuret having a melting point of 88°–89.5° C.

EXAMPLE 5

Synthesis of 1,1,3-trimethyl-5-phenylbiuret (Compound No. 6 in Table 1) by reaction process-B In 50 ml of anhydrous tetrahydrofuran, 7.4 g (0.08 mole) of aniline was dissolved. The mixture was cooled below 0° C., and a solution prepared by dissolving 6.4 g (0.04 mole) of 2,4,4-trimethylallophanoyl chloride in 10 ml of anhydrous tetrahydrofuran was added dropwise under stirring. The reaction was continued at a room temperature for 1 hour, then the solvent was removed by distillation under a reduced pressure, and water was added to form an insoluble matter. The insoluble matter was obtained by filtration and was recrystallized from ethanol to obtain 13.0 g (yield 73%) of 1,1,3-trimethyl-5-phenylbiuret having a melting point 89.5°–90.5° C.

EXAMPLE 6

Synthesis of 1-ethyl-3,5-dimethyl-1-phenylbiuret (Compound No. 58 in Table 1) by reaction process-B In 30 ml of anhydrous ethyl ether, 6.2 g (0.2 mole) of methyl amine was dissolved and cooled below 0° C. Then a solution prepared by dissolving 24.1 g (0.1 mole) of 4-ethyl-2-methyl-4-phenylallophanoyl chloride in 80 ml of anhydrous dichloroethane was added dropwise under stirring. The reaction was continued at a room temperature for 1 hour, the reaction mixture was washed with water and dried with anhydrous sodium sulfate. The solvent was removed by distillation to obtain a residue, and the residue was recrystallized from ether-petroleum ether to obtain 17.6 g (yield 75%) of 1-ethyl-3,5-dimethyl-1-phenylbiuret having a melting point of 57°–58° C.

EXAMPLE 7

Synthesis of 1,1-dimethyl-3,5-diphenylbiuret (Compound No. 42 in Table 1) by reaction process-C In 30 ml of acetonitrile, 0.025 mole of 1,3-diphenyl-1,3-diazetidine-2,4-dione was added, then 4.5 ml (0.05 mole) of dimethylamine aqueous solution (50%) was added dropwise under stirring. The reaction was continued at 50° C. for 0.5 hours and the solvent was removed by distillation under a reduced pressure to obtain a residue. The residue was recrystallized from ethanol to obtain 5.4 g (yield 76%) of 1,1-dimethyl-3,5-diphenylbiuret having a melting point of 105°–107° C.

In the following Table 1, there are mentioned the physico-chemical properties of 1,1,3,5-substituted biuret compounds of the formula (1) including the compounds prepared in Examples 1–7.

TABLE 1

| Compound No. | $R^1$ | $R^2$ | $R^3$ | $R^4$ | Reaction process | MP (°C.) | UV$\lambda_{max}^{Cyclohexane}$ M$\mu$ ($\epsilon$) | Molecular formula | Elemental Analysis (%) Calculated found | | |
|---|---|---|---|---|---|---|---|---|---|---|---|
| | | | | | | | | | C | H | N |
| 1* | —$CH_3$ | —$CH_3$ | —H |  | A-1 | 180.5–181 | 242.5(18700) | $C_{10}H_{13}N_3O_2$ | 57.96 (57.84) | 6.32 (6.56) | 20.28 (20.39) |

$R^1$—N—C—N—C—NH—$R^4$
   |    ‖    |    ‖
   $R^2$  O  $R^3$  O

TABLE 1-continued $R^1-N(R^2)-C(=O)-N(R^3)-C(=O)-NH-R^4$

| Compound No. | R¹ | R² | R³ | R⁴ | Reaction process | MP (°C.) | UV λ$_{max}^{Cyclohexane}$ Mμ (ε) | Molecular formula | Elemental Analysis (%) Calculated (found) C | H | N |
|---|---|---|---|---|---|---|---|---|---|---|---|
| 2 | —CH₃ | —CH₃ | —H | 4-F-C₆H₄ | A-1 | 182–185 (Sublimated) | 240(21600) | C₁₀H₁₂FN₃O₂ | 53.33 (53.51) | 5.37 (5.51) | 18.66 (18.83) |
| 3* | —CH₃ | —CH₃ | —H | 4-Cl-C₆H₄ | A-1 | 212–213.5 | 247(20900) | C₁₀H₁₂ClN₃O₂ | 49.70 (49.72) | 5.00 (5.01) | 17.39 (17.45) |
| 4 | —CH₃ | —CH₃ | —H | 4-OCH₃-C₆H₄ | A-1 | 156–158 | 249.5(20200) | C₁₁H₁₅N₃O₃ | 56.69 (55.61) | 6.37 (6.41) | 17.71 (17.37) |
| 5* | —CH₃ | —CH₃ | —H | 4-CH₃-C₆H₄ | A-1 | 186–190 | 245(18300) | C₁₁H₁₅N₃O₂ | 59.71 (59.50) | 6.83 (6.83) | 18.99 (18.92) |
| 6 | —CH₃ | —CH₃ | —CH₃ | C₆H₅ | B | 89.5–90.5 | 245(17800) | C₁₁H₁₅N₃O₂ | 59.71 (59.79) | 6.83 (6.92) | 18.99 (18.75) |
| 7 | —CH₃ | —CH₃ | —CH₃ | 2-F-C₆H₄ | B | 66.5–68 | 241.5(19200) | C₁₁H₁₄FN₃O₂ | 55.22 (55.28) | 5.90 (5.91) | 17.56 (17.42) |
| 8 | —CH₃ | —CH₃ | —CH₃ | 4-F-C₆H₄ | B | 73.5–74.5 | 241.5(15800) | C₁₁H₁₄FN₃O₂ | 55.22 (55.17) | 5.90 (6.04) | 17.56 (17.39) |
| 9 | —CH₃ | —CH₃ | —CH₃ | C₆F₄ | B | 103.5–105 | 232(15600) | C₁₁H₁₁F₄N₃O₂ | 45.06 (44.87) | 3.78 (3.84) | 14.33 (14.11) |
| 10 | —CH₃ | —CH₃ | —CH₃ | 2-Cl-C₆H₄ | A-2 | 89.5–91 | 247(16400) | C₁₁H₁₄ClN₃O₂ | 51.70 (51.59) | 5.52 (5.59) | 16.43 (16.39) |
| 11 | —CH₃ | —CH₃ | —CH₃ | 3-Cl-C₆H₄ | A-2 | 87–89 | 247(19000) | C₁₁H₁₄ClN₃O₂ | 51.70 (51.46) | 5.52 (5.51) | 16.43 (16.23) |
| 12 | —CH₃ | —CH₃ | —CH₃ | 4-Cl-C₆H₄ | A-2 | 94.5–95 | 250(22700) | C₁₁H₁₄ClN₃O₂ | 51.70 (51.63) | 5.52 (5.56) | 16.43 (16.55) |
| 13 | —CH₃ | —CH₃ | —CH₃ | 2,4-Cl₂-C₆H₃ | B | 69.5–70 | 253(23400) | C₁₁H₁₃Cl₂N₃O₂ | 45.54 (45.46) | 4.52 (4.57) | 14.48 (14.47) |
| 14 | —CH₃ | —CH₃ | —CH₃ | 3,4-Cl₂-C₆H₃ | B | 123–124 | 253(23900) | C₁₁H₁₃Cl₂N₃O₂ | 45.54 (45.33) | 4.52 (4.52) | 14.48 (14.48) |
| 15 | —CH₃ | —CH₃ | —CH₃ | 2,3-Cl₂-C₆H₃ | B | 140–141 | 235 sh. | C₁₁H₁₃Cl₂N₃O₂ | 45.54 (45.58) | 4.52 (4.36) | 14.48 (14.56) |
| 16 | —CH₃ | —CH₃ | —CH₃ | 4-Br-C₆H₄ | B | 105–106 | 252(24500) | C₁₁H₁₄BrN₃O₂ | 44.02 (43.67) | 4.70 (4.73) | 14.00 (13.91) |
| 17 | —CH₃ | —CH₃ | —CH₃ | 2-CF₃-C₆H₄ | B | 72–73 | 244(16700) | C₁₂H₁₄F₃N₃O₂ | 49.83 (49.84) | 4.88 (4.89) | 14.53 (14.14) |
| 18 | —CH₃ | —CH₃ | —CH₃ | 3-CF₃-C₆H₄ | B | 69–69.5 | 245(21100) | C₁₂H₁₄F₃N₃O₂ | 49.83 (49.83) | 4.88 (4.64) | 14.53 (14.46) |
| 19 | —CH₃ | —CH₃ | —CH₃ | 4-N(CH₃)₂-C₆H₄ | B | 124–126 | 273(20600) | C₁₃H₂₀N₄O₂ | 59.07 (59.32) | 7.63 (7.56) | 21.20 (21.08) |
| 20 | —CH₃ | —CH₃ | —CH₃ | 4-NO₂-C₆H₄ | B | 157–159 | 310(15400) | C₁₁H₁₄N₄O₂ | 49.62 (49.63) | 5.30 (5.33) | 21.04 (21.06) |
| 21 | —CH₃ | —CH₃ | —CH₃ | 4-OH-C₆H₄ | B | 119–120 | 253(12500) | C₁₁H₁₅N₃O₃ | 55.69 (55.87) | 6.37 (6.56) | 17.71 (17.42) |

TABLE 1-continued $$R^1-N(R^2)-C(=O)-N(R^3)-C(=O)-NH-R^4$$

| Compound No. | R¹ | R² | R³ | R⁴ | Reaction process | MP (°C.) | UV λmax Cyclohexane Mμ (ε) | Molecular formula | Elemental Analysis (%) Calculated (found) C | H | N |
|---|---|---|---|---|---|---|---|---|---|---|---|
| 22 | —CH₃ | —CH₃ | —CH₃ | 2-methoxyphenyl (H₃CO-C₆H₄—) | B | 112–113.5 | 247(16000) | $C_{12}H_{17}N_3O_3$ | 57.36 (57.57) | 6.82 (6.86) | 16.72 (16.58) |
| 23 | —CH₃ | —CH₃ | —CH₃ | 4-methoxyphenyl | B | 87.5–89 | 250.5(17500) | $C_{12}H_{17}N_3O_3$ | 57.36 (57.49) | 6.82 (6.83) | 16.72 (16.50) |
| 24 | —CH₃ | —CH₃ | —CH₃ | 3,4-dimethoxyphenyl | B | 96.5–98.5 | 253.5(13100) | $C_{13}H_{19}N_3O_4$ | 55.50 (55.22) | 6.81 (6.94) | 14.94 (14.72) |
| 25 | —CH₃ | —CH₃ | —CH₃ | 3,4,5-trimethoxyphenyl | B | 133–135 | 256(14300) | $C_{14}H_{21}N_3O_5$ | 54.01 (54.00) | 6.80 (7.09) | 13.50 (13.54) |
| 26 | —CH₃ | —CH₃ | —CH₃ | 2-methylphenyl | B | 59.5–60 | 246(15200) | $C_{12}H_{17}N_3O_2$ | 61.26 (61.28) | 7.28 (7.48) | 17.86 (17.76) |
| 27 | —CH₃ | —CH₃ | —CH₃ | 3-methylphenyl | B | 98–99 | 246(17100) | $C_{12}H_{17}N_3O_2$ | 61.26 (61.39) | 7.28 (7.43) | 17.86 (17.76) |
| 28 | —CH₃ | —CH₃ | —CH₃ | 4-methylphenyl | B | 115–117 | 247.5(18800) | $C_{12}H_{17}N_3O_2$ | 61.26 (61.38) | 7.28 (7.15) | 17.86 (17.69) |
| 29 | —CH₃ | —CH₃ | —CH₃ | 2,3-dimethylphenyl | B | 104–105 | 247(13100) | $C_{13}H_{19}N_3O_2$ | 62.63 (62.87) | 7.68 (7.96) | 16.85 (16.80) |
| 30 | —CH₃ | —CH₃ | —CH₃ | 2,3-dimethylphenyl (isomer) | B | 115–117 | 248(25400) | $C_{13}H_{19}N_3O_2$ | 62.63 (62.71) | 7.68 (8.00) | 16.85 (16.67) |
| 31 | —CH₃ | —CH₃ | —CH₃ | 3,5-dimethylphenyl | B | 102–105 | 227 sh. | $C_{13}H_{19}N_3O_2$ | 62.63 (62.66) | 7.68 (7.75) | 16.85 (16.80) |
| 32 | —CH₃ | —CH₃ | —CH₃ | 2-methyl-3-chlorophenyl | B | 102–103 | 247.5(15400) | $C_{12}H_{16}ClN_3O_2$ | 53.44 (53.20) | 5.98 (6.06) | 15.58 (15.58) |
| 33 | —CH₃ | —CH₃ | —CH₃ | 4-acetylphenyl (—C₆H₄—COCH₃) | B | 110–112 | 283(25800) | $C_{13}H_{17}N_3O_3$ | 59.30 (59.30) | 6.51 (6.65) | 15.96 (15.82) |
| 34 | —CH₃ | —CH₃ | —CH₃ | 4-methylthiophenyl (—C₆H₄—SCH₃) | B | 59–61 | 282(20700) | $C_{12}H_{17}N_3O_2S$ | 53.91 (53.72) | 6.41 (6.44) | 15.72 (15.90) |
| 35 | —CH₃ | —CH₃ | —CH₃ | cyclohexyl | B | 79–80 | | $C_{11}H_{21}N_3O_2$ | 58.12 (57.95) | 9.31 (9.60) | 18.49 (18.15) |
| 36 | —CH₃ | —CH₃ | —C₂H₅ | phenyl | B | 104.5–106.5 | 245(16800) | $C_{12}H_{17}N_3O_2$ | 61.26 (61.61) | 7.28 (7.55) | 17.86 (18.05) |
| 37 | —CH₃ | —CH₃ | —(CH₂)₂CH₃ | phenyl | B | 102–104.5 | 245(17600) | $C_{13}H_{19}N_3O_2 \cdot \tfrac{1}{4}H_2O$ | 61.52 (61.51) | 7.75 (7.94) | 16.56 (16.65) |
| 38 | —CH₃ | —CH₃ | —(CH₂)₃CH₃ | phenyl | B | 92–93.5 | 245(14100) | $C_{14}H_{21}N_3O_2$ | 63.86 (63.85) | 8.04 (8.47) | 15.96 (15.97) |
| 39 | —CH₃ | —CH₃ | phenyl | —CH₃ | B | 98–99.5 | 230(7800) | $C_{11}H_{15}N_3O_2$ | 59.71 (59.70) | 6.83 (6.97) | 18.99 (18.60) |
| 40 | —CH₃ | —CH₃ | phenyl | —(CH₂)₃CH₃ | B | Oily product | | $C_{14}H_{21}N_3O_2$ | (a) | | |
| 41 | —CH₃ | —CH₃ | phenyl | cyclohexyl | B | 73.5–75 | | $C_{16}H_{23}N_3O_2$ | 66.41 (66.32) | 8.01 (8.11) | 14.52 (14.36) |

TABLE 1-continued $$R^1-\underset{\underset{O}{\|}}{\overset{R^2}{N}}-C-\underset{\underset{O}{\|}}{\overset{R^3}{N}}-C-NH-R^4$$

| Compound No. | $R^1$ | $R^2$ | $R^3$ | $R^4$ | Reaction process | MP (°C.) | UV$\lambda_{max}^{Cyclohexane}$ M$\mu$ ($\epsilon$) | Molecular formula | Elemental Analysis (%) Calculated (found) C | H | N |
|---|---|---|---|---|---|---|---|---|---|---|---|
| 42* | —CH$_3$ | —CH$_3$ | —Ph | —Ph | C | 105–107 | | C$_{16}$H$_{17}$N$_3$O$_2$ | 67.83 (67.83) | 6.05 (5.92) | 14.83 (14.36) |
| 43 | —CH$_3$ | —C$_2$H$_5$ | —H | —Ph | A-1 | 157–159 | 243(20800) | C$_{11}$H$_{15}$N$_3$O$_2$ | 59.71 (59.53) | 6.83 (6.60) | 18.99 (18.61) |
| 44 | —CH$_3$ | —C$_2$H$_5$ | —H | —CH$_2$—Ph | A-2 | 100–101 | | C$_{12}$H$_{17}$N$_3$O$_2$ | 61.26 (61.42) | 7.28 (7.44) | 17.86 (17.53) |
| 45 | —CH$_3$ | —C$_2$H$_5$ | —CH$_3$ | —Ph | A-2 | 88.5–90.5 | 244.5(13400) | C$_{12}$H$_{17}$N$_3$O$_2$ | s,7 61.26 (61.25) | 7.28 (7.44) | 17.86 (17.61) |
| 46 | —CH$_3$ | —(CH$_2$)$_2$CH$_3$ | —CH$_3$ | —Ph | A-2 | 63–64 | 244(19200) | C$_{13}$H$_{19}$N$_3$O$_2$ | 62.63 (62.84) | 7.68 (7.65) | 16.85 (16.88) |
| 47 | —CH$_3$ | —(CH$_2$)$_3$CH$_3$ | —H | —Ph | A-1 | 68–70 | 240(19200) | C$_{13}$H$_{19}$N$_3$O$_2$ | 62.63 (62.59) | 7.68 (7.68) | 16.85 (16.65) |
| 48 | —CH$_3$ | —(CH$_2$)$_2$CH$_3$ | —CH$_3$ | —Ph | A-3 | Oily product | | C$_{14}$H$_{21}$N$_3$O$_2$ | (b) | | |
| 49 | —CH$_3$ | —Ph | —H | —CH$_3$ | A-3 | 123–125 | 234(5500) | C$_{10}$H$_{13}$N$_3$O$_2$ | 57.96 (58.11) | 6.32 (6.48) | 20.28 (20.22) |
| 50 | —CH$_3$ | —Ph | —H | —C$_2$H$_5$ | A-3 | 68–70 | 236(5400) | C$_{11}$H$_{15}$N$_3$O$_2$ | 59.71 (59.55) | 6.83 (7.08) | 18.99 (19.02) |
| 51 | —CH$_3$ | —Ph | —H | —(CH$_2$)$_2$CH$_3$ | A-3 | 28–30 | | C$_{12}$H$_{17}$N$_3$O$_2$ | 61.26 (61.13) | 7.28 (7.24) | 17.86 (17.92) |
| 52 | —CH$_3$ | —Ph | —H | —(CH$_2$)$_3$CH$_3$ | A-3 | 45–46 | 235(5700) | C$_{13}$H$_{19}$N$_3$O$_2$ | 62.63 (62.68) | 7.68 (7.83) | 16.85 (16.95) |
| 53* | —CH$_3$ | —Ph | —CH$_3$ | —CH$_3$ | B | 109–110 | 244(10300) | C$_{11}$H$_{15}$N$_3$O$_2$ | 59.71 (59.81) | 6.83 (6.96) | 18.99 (18.93) |
| 54 | —CH$_3$ | —Ph | —CH$_3$ | —C$_2$H$_5$ | B | Oily product | | C$_{12}$H$_{17}$N$_3$O$_2$ | (c) | | |
| 55 | —CH$_3$ | —Ph | —CH$_3$ | —(CH$_2$)$_2$CH$_3$ | B | Oily product | | C$_{13}$H$_{19}$N$_3$O$_2$ | (d) | | |
| 56 | —CH$_3$ | —Ph | —CH$_3$ | —CH(CH$_3$)$_2$ | B | Oily product | | C$_{13}$H$_{19}$N$_3$O$_2$ | (e) | | |
| 57 | —C$_2$H$_5$ | —C$_2$H$_5$ | —CH$_3$ | —Ph | A-3 | 88–89.5 | 244(18900) | C$_{13}$H$_{19}$N$_3$O$_2$ | 62.63 (62.71) | 7.68 (7.61) | 16.85 (16.86) |
| 58 | —C$_2$H$_5$ | —Ph | —CH$_3$ | —CH$_3$ | B | 57–58 | 245.5(10200) | C$_{12}$H$_{17}$N$_3$O$_2$ | 61.26 (60.84) | 7.28 (7.34) | 17.86 (17.70) |
| 59 | —C$_2$H$_5$ | —Ph(Cl) | —CH$_3$ | —CH$_3$ | B | 82–83 | 244(8200) | C$_{12}$H$_{16}$ClN$_3$O$_2$ | 63.43 (53.68) | 5.98 (6.07) | 15.58 (15.44) |
| 60 | —C$_2$H$_5$ | —Ph(Cl) | —CH$_3$ | —CH$_3$ | B | Oily product | | C$_{12}$H$_{16}$ClN$_3$O$_2$ | (f) | | |
| 61 | —C$_2$H$_5$ | —Ph(OCH$_3$) | —CH$_3$ | —CH$_3$ | B | Oily product | | C$_{13}$H$_{19}$N$_3$O$_3$ | (g) | | |
| 62 | —C$_2$H$_5$ | —Ph(CH$_3$) | —CH$_3$ | —CH$_3$ | B | Oily product | | C$_{13}$H$_{19}$N$_3$O$_2$ | (h) | | |
| 63 | —(CH$_2$)$_2$CH$_3$ | —Ph | —CH$_3$ | —CH$_3$ | A-2 | 60–61 | | C$_{13}$H$_{19}$N$_3$O$_2$ | 62.63 (62.60) | 7.68 (7.56) | 16.85 (16.76) |
| 64 | —(CH$_2$)$_3$CH$_3$ | —Ph | —CH$_3$ | —CH$_3$ | A-2 | Oily product | | C$_{14}$H$_{21}$N$_3$O$_2$ | (i) | | |
| 65 | —Ph | —Ph | —CH$_3$ | —CH$_3$ | A-2 | 151–152 | 251(15500) | C$_{16}$H$_{17}$N$_3$O$_2$ | 67.83 (67.83) | 6.05 (6.18) | 14.83 (14.85) |

TABLE 1-continued $$R^1-N(R^2)-C(=O)-N(R^3)-C(=O)-NH-R^4$$

| Compound No. | R¹ | R² | R³ | R⁴ | Reaction process | MP (°C.) | UV$\lambda_{max}^{Cyclohexane}$ M$\mu$ ($\epsilon$) | Molecular formula | Elemental Analysis (%) Calculated (found) C | H | N |
|---|---|---|---|---|---|---|---|---|---|---|---|
| 66 | cyclobutyl | | —CH₃ | —C₆H₅ | B | 109.5–110.5 | 248.5(15700) | C₁₁H₁₃N₃O₂ | 60.26 (60.29) | 5.98 (5.85) | 19.17 (19.08) |
| 67 | cyclopentyl | | —H | —C₆H₅ | A-1 | 174.5–176.5 | 243(21400) | C₁₂H₁₅N₃O₂ | 61.79 (61.69) | 6.48 (6.69) | 18.01 (18.11) |
| 68 | cyclopentyl | | —CH₃ | —C₆H₅ | B | 77–78 | 245(19000) | C₁₃H₁₇N₃O₂ | 63.14 (63.15) | 6.93 (7.10) | 16.99 (17.06) |
| 69 | cyclohexyl | | —H | —C₆H₅ | A-1 | 163–165 | | C₁₃H₁₇N₃O₂ | 63.14 (63.20) | 6.93 (6.91) | 16.99 (17.10) |
| 70 | cyclohexyl | | —CH₃ | —C₆H₅ | B | 57–58 | 246(18600) | C₁₄H₁₉N₃O₂ | 64.35 (64.31) | 7.33 (7.42) | 16.08 (15.82) |
| 71 | morpholino | | —H | —C₆H₅ | A-1 | 196–199 | | C₁₂H₁₅N₃O₃ | 57.82 (58.00) | 6.06 (6.10) | 16.85 (16.88) |
| 72 | morpholino | | —CH₃ | —CH₃ | B | Oily product | | C₈H₁₅N₃O₃ | j | | |
| 73 | morpholino | | —CH₃ | —C₆H₅ | B | 122–123 | 246(18000) | C₁₃H₁₇N₃O₃ | 59.30 (59.28) | 6.51 (6.27) | 15.96 (15.93) |

In Table 1, the compounds with * marks are known compounds and thus the remaining compounds are novel. Further, in compounds Nos. 40, 48, 54, 55, 56, 60, 61, 62, 64 and 72, under column of Elementary analysis, ⓐ, ⓑ, ⓒ, ⓓ, ⓔ, ⓕ, ⓖ, ⓗ, ⓘ and ⓙ indicate the following data obtained by NMR and mass-spectrography methods in place of data obtained by elemental analysis. ⓐ NMR(CDCl₃) δ: 0.91 (3H, m, N₁—CH₂CH₂CH₂—C$\underline{H}$₃), 1.05–1.68 (4H, m, N₁—CH₂—C$\underline{H}$₂C$\underline{H}$₂—CH₃), 2.82 (6H, s,

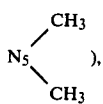

3.25 (2H, q, J=6.0 Hz, N₁—C$\underline{H}$₂—CH₂CH₂CH₃), 6.39 (1H, broad, N₁—$\underline{H}$), 7.15–7.56 (5H, m, Ar—H), MS m/e: 263 (M+). ⓑ NMR (CDCl₃) δ: 0.94 (3H, m, N₁—CH₂CH₂CH₂—C$\underline{H}$₃), 1.07–1.80 (4H, m, N₁—CH₂—C$\underline{H}$₂C$\underline{H}$₂—CH₃), 2.90 (3H, s, N₁—CH₃), 3.12 (3H, s, N₃—CH₃), 3.24 (2H, q, J=8.0 Hz, N₁—C$\underline{H}$₂—CH₂CH₂CH₃), 6.85–7.51 (5H, m, Ar-H), 9.47 (1H, broad s, N₅—H). MS m/e: 263 (M+), ⓒ NMR(CDCl₃) δ: 1.12 (3H, t, J=7.0 Hz, N₁—CH₂—C$\underline{H}$₃), 2.54 (3H, s, N₃—CH₃), 3.23 (3H, s, N₅—CH₃), 3.27 (2H, m J=7.0 Hz, N₁—C$\underline{H}$₂—CH₃), 6.96–7.45 (5H, m, Ar—H), 7.97 (1H, broad, N₁—H). MS m/e: 235 (M+). ⓓ NMR(CDCl₃) δ: 0.91 (3H, t, J=7.0 Hz, N₅—CH₂C$\underline{H}$₂—CH₃), 1.52 (2H, m, J=7.0 Hz, N₅—C$\underline{H}$₂—CH₂—CH₃), 2.55 (3H, s, N₃—CH₃), 3.24 (3H, s, N₁—CH₃), 3.22 (2H, q, J=7.0 Hz, N₅—C$\underline{H}$₂—CH₂CH₃), 6.90–7.40 (5H, m, Ar—H), 8.05 (1H, broad, N₅—H). MS m/e: 249 (M+). ⓔ NMR(CDCl₃) δ: 1.14 (6H, d, J=7.0 Hz, —HC(C$\underline{H}$₃)₂), 2.54 (3H, s, N₃—CH₃), 3.22 (3H, s, N₁—CH₃), 3.90 (1H, m, J=7.0 Hz, N₅—C$\underline{H}$(CH₃)₂), 7.00–7.40 (5H, m, Ar—H), 7.94 (1H broad d, N₅—H). MS m/e: 249 (M+). ⓕ NMR(CDCl₃) δ: 1.10 (3H, t, J=7.0 Hz, N₁—CH₂—C$\underline{H}$₃), 2.58 (3H, s, N₃—CH₃), 2.82 (3H, d, J=5.0 Hz, N₅—CH₃), 3.68 (2H, q, J=7.0 Hz, N₁—C$\underline{H}$₂—CH₃), 6.82–7.49 (4H, m, Ar—H), 7.88 (1H, broad, N₅—H). MS m/e: 269 (M+). ⓖ NMR(CDCl₃) δ: 1.10 (3H, t, J=7.0 Hz, N₁—CH₂—C$\underline{H}$₃), 2.53 (3H, s, N₃—CH₃), 2.80 (3H, d, J=5.0 Hz, N₅—CH₃), 3.64 (2H, q, J=7.0 Hz, N₁—C$\underline{H}$₂—CH₃). 3.75 (3H, s, O—CH₃), 6.71–7.09 (4H, m, Ar—H), 7.85 (1H, broad, N₅—H). MS m/e: 265 (M+). ⓗ NMR(CDCl₃) δ: 1.10 (3H, t, J=7.0 Hz, N₁—CH₂—C$\underline{H}$₃), 2.30 (3H, s, Ar—CH₃), 2.53 (3H, s, N₃—CH₃), 2.81 (3H, d, J=5.0 Hz, N₅—CH₃), 3.67 (2H, q, J=7.0 Hz, N₁—C$\underline{H}$₂—CH₃), 6.75–7.25 (4H, m, Ar—H), 7.89 (1H, broad, N₅—H). MS m/e: 249 (M+). ⓘ NMR(CDCl₃) δ: 0.85 (3H, m, J=6.0 Hz, N₁—CH₂CH₂CH₂—C$\underline{H}$₃), 1.02–1.85 (4H, m, N₁—CH₂—C$\underline{H}$₂C$\underline{H}$₂—CH₃), 2.52 (3H, s, N₃—CH₃). 2.81 (3H, d, J=4.0 Hz, N₅—CH₃), 3.63 (2H, t, J=6.0 Hz, N₁—C$\underline{H}$₂—CH₂CH₂CH₃), 6.90–7.50 (5H, m, Ar—H), 7.93 (1H, broad, N₅—H). MS m/e: 263 (M+). ⓙ NMR(CDCl₃) δ: 2.76 (3H, d, J=5.0 Hz, NH—CH₃), 3.05 (3H, s,

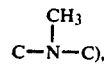

3.20–3.78 (8H, m, morpholine ring protons), 7.18 (1H, broad, N$\underline{\text{H}}$—CH$_3$), MS m/e: 201 (M+).

Next, several tests for determining the pharmacological properties, in that acute toxicity, antipyretic activity, analgesic activity and anti-inflammatory activity of the present 1,1,3,5-substituted biuret compounds of the formula (1) were conducted and the test results are shown in Table (2). In the tests, each compounds to be tested was used as a suspension in 0.25% carboxymethylcellulose solution. Methods for testing are explained as follows:

1. Acute toxicity

The ddy strain of male mice (body weight, 20–25 g) were used as test animals. The mice were fasted overnight and the compound to be tested was administered orally. General symptom of the mouse after the administration was observed for 7 days. The lethal dose (mg/kg, body weight) of the test compound was determined in connection with the death number of mice/the number of mice tested. In Table 2, the values indicated with Δ marks are 50% lethal dose, LD$_{50}$ (mg/kg, body weight).

2. Anti-pyretic activity

According to the method reported by Tanabe [Folia Pharmacologia Japonica, Vol. 73, pp. 803 (1977)], the Wistar strain of male rats (150–180 g, body weight) were used as test animals. The rats were fasted overnight, and 1 ml/100 g (body weight) of 10% dry-yeast suspension were subcutaneously injected on the back of the rats. Five hours after the injection, the test compound was administered orally, then the body temperature of the rat was measured at time sequences. Antipyretic activity of the test compound was determined as the FI (febril index) by integrating pyrogenetic curve up to 4 hours after the administration of the test compound with time, and indicated as inhibitory ratio (%) shown by the following formula, $$\text{Inhibitory ratio}(\%) = \left[1 - \frac{\left(\begin{array}{c}\text{FI of the test group of rats}\\ \text{administered with test compound}\end{array}\right)}{(\text{FI of control group of rats})}\right] \times 100$$

3. Analgesic activity (1) Acetic acid-induced stretching method

According to the method reported by Koster et. al., [Fed. Proc., Vol. 18, pp. 412 (1959)], the ddy strain of male mice (body weight, 20–25 g) were used as test animals. The mice were fasted overnight, 100 mg/kg body weight of the test compound was administered orally, then 1 hour after the administration, 0.2 ml of 0.7% acetic acid solution was injected intraperitoneally. The acetic acid-induced stretching symptom of mouse was observed. Analgesic activity of the test compound was calculated as the inhibitory ratio (%). In Table 2, the values in parentheses show the data obtained from the test by using the dosage other than 100 mg/kg body weight. Further, the values indicated with Δ marks show 50% effective dose, ED$_{50}$ (mg/kg body weight).

(2) Haffner method.

According to the modified method reported by Fujimura et. al., [Bulletin of the Institute for Chemical Research, Kyoto University, No. 25, pp. 36 (1951)], the ddy strain of male mice (body weight, 20–25 g) were used as test animals. The mice were fasted overnight, 100 mg/ig body weight of the test compound was administered orally, then 45 minutes after the administration, the threshold amount (1.5–2.5 mg/kg body weight) of morphine hydrochloride was injected subcutaneously. Then 1-hour pain reaction of the mouse caused by a clamp was observed. Analgesic activity of the test compound was calculated as the inhibitory ratio (%). In Table 2, the values in parentheses show the data obtained from the test by using the dosage other than 100 mg/kg body weight. Further, the values indicated with Δ marks show 50% effective dose, ED$_{50}$ (mg/kg body weight).

4. Anti-inflammatory activity.

According to the method of acute carrageenin-induced inflammatory test [Folia Pharmacologia Japonica, Vol. 56, pp. 575 (1960)], the Wistar strain of male rats (body weight, 150–180 g) were used as test animals. The rats were fasted overnight, 100 mg/kg body weight of the test compound was administered orally, then 1 hour after the administration, 0.1 ml of 1% carrageenin solution, as the inflammation inducing agent, was injected subcutaneously to the hindpaw of the rat and the volume of the hindpaw was measured at time sequences. Anti-inflammatory activity of the test compound was calculated as inflammation inhibitory ratio (%) at 3 hours after the injection of inflammation inducing agent.

TABLE 2

| Compound No. | Acute toxicity (mg/kg) | Analgesic activity (%) | | Anti-pyretic activity (%) | Anti-inflammatory activity (%) |
|---|---|---|---|---|---|
| | | Acetic acid-induced stretching method | Haffner method | | |
| 1* | 2000 - 0/4 | 50 | 50 (200 mg/kg) | | 42 |
| 2 | 2000 - 0/4 | 40 | | | |
| 3* | 2000 - 0/4 | 50 | | | |
| 4 | 2000 - 0/4 | 75 | 50 | | 43 |
| 5* | 2000 - 0/4 | 25 | | | 23 (2 hours) |
| 6 | Δ 1709 | Δ75(43–132) | Δ68(52–88) | 80 | 59 |
| 7 | 1000 - ¼ 2000 - 4/4 | 62.5 | 75 | 76 | 63 |
| 8 | Δ 930 | 87.5 | 62.5 | 61 | 37 |
| 9 | 500 - 0/4 1000 - 4/4 | 87.5 | 50 | 33 | 24 |
| 10 | 2000 - 0/4 | Δ135(71 –236) | 37.5 | 66 | 38 |
| 11 | Δ 1481 | 62.5 | 75 (200 mg/kg) | 43 | 30 (2 hours) |
| 12 | Δ 1200 | Δ12(4–36) | Δ20(11–35) | 84 | 47 |
| 13 | 1000 - 0/4 2000 - ¾ | 50 | 75 | 42 | |

TABLE 2-continued

| Compound No. | Acute toxicity (mg/kg) | Analgesic activity (%) Acetic acid-induced stretching method | Haffner method | Anti-pyretic activity (%) | Anti-inflammatory activity (%) |
|---|---|---|---|---|---|
| 14 | 1000 - 1/4<br>2000 - 3/4 | 50 | 62.5 | 43 | |
| 15 | Δ 1100 | 50 | 50 | 29 | 25 |
| 16 | Δ 1353 | Δ60(48–76) | Δ74(49–113) | 103 | 48<br>(2 hours) |
| 17 | 1000 - 1/4 | 12.5 | 37.5 | 65 | 66 |
| 18 | 1000 - 0/4<br>2000 - 4/4 | 37.5 | Δ64(37–112) | 62 | 32<br>(2 hours) |
| 19 | 2000 - 0/4 | 62.5 | 50 | 26 | 32<br>(2 hours) |
| 20 | 500 - 2/4 | 100 | 50 | 26 | 32 |
| 21 | 1000 - 0/4<br>2000 - 3/4 | 37.5 | 12.5 | | |
| 22 | 1000 - 0/4<br>2000 - 2/4 | 37.5 | 50 | 13 | 35<br>(2 hours) |
| 23 | Δ 1800 | Δ39(21–73) | Δ80(42–153) | 75 | 33 |
| 24 | 1000 - 0/4<br>2000 - 4/4 | 75 | 62.5 | 18 | |
| 25 | 500 - 0/4<br>1000 - 2/4 | Δ38(18–80) | 62.5 | 23 | 30 |
| 26 | Δ 1000 | 37.5 | 50 | 41 | 29 |
| 27 | 2000 - 2/4 | 75 | 37.5 | 31 | 28 |
| 28 | 2000 - 0/4 | Δ33(14–78) | Δ80(42–152) | 52 | 23<br>(2 hours) |
| 29 | 1000 - 1/4<br>2000 - 4/4 | 50 | 25 | 40 | |
| 30 | 2000 - 1/4 | 87.5<br>(60 mg/kg) | Δ86(57–129) | 31 | |
| 31 | Δ 595 | 75 | 37.5 | 69 | |
| 32 | 1000 - 1/4<br>2000 - 4/4 | 75 | 25 | 45 | |
| 33 | 500 - 0/4<br>1000 - 4/4 | 62.5 | 37.5 | 36 | 31<br>(2 hours) |
| 34 | 1000 - 0/4<br>2000 - 4/4 | 50 | | | |
| 35 | Δ 1447 | 87.5<br>(200 mg/kg) | 25 | | 24<br>(2 hours) |
| 36 | 1000 - 0/4<br>2000 - 3/4 | 62.5 | 62.5 | 12 | 23 |
| 37 | 2000 - 0/4 | 37.5 | 62.5<br>(200 mg/kg) | 12 | |
| 38 | 1000 - 0/4<br>200 - 3/4 | 37.5 | 37.5<br>(200 mg/kg) | 18 | 31 |
| 39 | Δ 93 | 25<br>(50 mg/kg) | 25<br>(50 mg/kg) | | 33<br>(25 mg/kg) |
| 40 | 1000 - 0/4<br>2000 - 1/4 | 62.5<br>(200 mg/kg) | 62.5 | | |
| 41 | Δ 1276 | 50<br>(200 mg/kg) | 62.5 | | |
| 42* | 1000 - 0/4<br>200 - 3/4 | 62.5<br>(200 mg/kg) | 50<br>(200 mg/kg) | 14 | 34 |
| 43 | 2000 - 0/4 | 50 | 12.5<br>(200 mg/kg) | | 72<br>(200 mg/kg) |
| 44 | Δ 1400 | 87.5<br>(200 mg/kg) | | | 47<br>(200 mg/kg) |
| 45 | Δ 1288 | 50<br>(80 mg/kg) | Δ100(59–170) | 49 | 34 |
| 46 | 1000 - 1/4<br>2000 - 4/4 | 75<br>(60 mg/kg) | 37.5 | 44 | 26<br>(2 hours) |
| 47 | 2000 - 0/4 | 50 | 25 | | 20 |
| 48 | 1000 - 0/4<br>2000 - 3/4 | 37.5 | 25 | 35 | |
| 49 | Δ 1605 | Δ34(16–79) | Δ86(41–183) | 48 | 32 |
| 50 | Δ 1960 | 50 | 37.5 | 90 | 38 |
| 51 | 500 - 1/4<br>1000 - 2/4 | 37.5 | 87.5 | 164 | 60 |
| 52 | 1000 - 0/4<br>2000 - 3/4 | 62.5 | 50 | 104 | 48 |
| 53* | Δ 1349 | Δ68(30–152) | Δ135(63–291) | 108 | 76 |
| 54 | Δ 1350 | 37.5 | 75 | 58 | 54 |
| 55 | 1000 - 1/4<br>1500 - 4/4 | Δ80(44–147) | Δ90(60–134) | 80 | 73 |
| 56 | Δ 1325 | 25 | 12.5 | 65 | 47 |
| 57 | 2000 - 1/4 | 37.5 | 50<br>(200 mg/kg) | 19 | 23 |
| 58 | Δ 1000 | 75 | 62.5 | 137 | 60 |
| 59 | Δ 810 | 37.5 | 12.5 | 64 | 51<br>(2 hours) |

TABLE 2-continued

| Compound No. | Acute toxicity (mg/kg) | Analgesic activity (%) Acetic acid-induced stretching method | Haffner method | Anti-pyretic activity (%) | Anti-inflammatory activity (%) |
|---|---|---|---|---|---|
| 60 | 1000 - 1/4<br>2000 - 3/4 | 75 | 50 | 88 | 33 |
| 61 | Δ 1252 | 75 | 25 | 35 | 52 |
| 62 | Δ 1481 | 62.5 | 37.5 | 18 | |
| 63 | 1000 - 3/4<br>2000 - 4/4 | 50 | 50 | 76 | 58 |
| 64 | 500 - 1/4<br>1000 - 2/4 | 25 | 37.5 | 50 | 43 |
| 65 | 1000 - 1/4<br>2000 - 4/4 | 12.5 | 50 | | |
| 66 | 250 - 2/4<br>500 - 4/4 | 62.5 | 25 | 28 | |
| 67 | 2000 - 0/4 | 50 | 37.5 | | 33 |
| 68 | 2000 - 2/4 | 75 | | 24 | |
| 69 | 2000 - 0/4 | 50 | Δ115(66-200) | | |
| 70 | Δ 515 | 62.5 (200 mg/kg) | 37.5 | | |
| 71 | 2000 - 0/4 | 40 (200 mg/kg) | 50 (200 mg/kg) | | 23 (200 mg/kg) |
| 72 | 2000 - 0/4 | 50 | 25 | | |
| 73 | 2000 - 0/4 | 50 | 25 | 17 | |

The followings are examples of preparations for analgesic, anti-pyretic or anti-inflammatory composition containing 1,1,3,5-substituted biuret compound of the formula (1) as the active ingredient.

PREPARATION 1

| Ingredients | Amount (mg) |
|---|---|
| 1,1,3-Trimethyl-5-phenylbiuret (Compound No. 6) | 200 |
| Lactose | 500 |
| Corn starch | 280 |
| Hydroxypropylcellulose | 20 |
| To make one package contains | 1,000 |

By using the ingredients in the above-mentioned formulation, granular preparation is prepared by common method.

PREPARATION 2

| Ingredients | Amount (mg) |
|---|---|
| 1,1,3-Trimethyl-5-(4-chlorophenyl)biuret (Compound No. 12) | 100 |
| Lactose | 85 |
| Crystalline cellulose | 50 |
| Hydroxypropylstarch | 30 |
| Talc | 4 |
| Magnesium stearate | 1 |
| To make one tablet contains | 270 |

By using the ingredients in the above-mentioned formulation, tablet preparation is prepared by common method.

PREPARATION 3

| Ingredients | Amount (mg) |
|---|---|
| 1,1,3-Trimethyl-5-(4-bromophenyl)-biuret (Compound No. 16) | 100 |
| Lactose | 50 |
| Potate starch | 50 |
| Crystalline cellulose | 109 |

-continued

| Ingredients | Amount (mg) |
|---|---|
| Magnesium stearate | 1 |
| To make one capsule contains | 310 |

By using the ingredients in the above-mentioned formulation, a capsule preparation is prepared by common method.

PREPARATION 4

| Ingredients | Amount (mg) |
|---|---|
| 1,1,3-Trimethyl-5-(4-methoxyphenyl)biuret (Compound No. 23) | 200 |
| Lactose | 100 |
| Crystalline cellulose | 98 |
| Magnesium stearate | 2 |
| To make one capsule contains | 400 |

By using the ingredients in the above-mentioned formulation, a capsule preparation is prepared by common method.

PREPARATION 5

| Ingredients | Amounts (mg) |
|---|---|
| 1,1,3-Trimethyl-5-(4-methylphenyl)biuret (Compound No. 28) | 250 |
| Witepzol W-35 (A trade name for a suppository base material manufactured by and sold from Dynamite Nobel Company.) | 750 |
| To make one suppository contains | 1,000 |

By using the ingredients in the above-mentioned formulation, a suppository preparation is prepared by common method.

PREPARATION 6

| Ingredients | Amounts (mg) |
| --- | --- |
| 1,1,3-Trimethyl-5-(3,4-dimethyl-phenyl)biuret (Compound No. 30) | 100 |
| Sodium chloride | 16 |
| Distilled water for injection | q.s. |
| To make one ampule contains | 2 ml |

By using the ingredients in the above-mentioned formulation, an injection preparation (ampule) is prepared by common method.

PREPARATION 7

| Ingredients | Amounts (g) |
| --- | --- |
| 1,3,5-Trimethyl-1-phenylbiuret (Compound No. 53) | 2.0 |
| White vaseline | 23.0 |
| Stearyl alcohol | 22.0 |
| Propylene glycol | 12.0 |
| Sodium laurylsulfate | 1.5 |
| Ethyl p-oxybenzoate | 0.025 |
| Propyl p-oxybenzoete | 0.015 |
| Purified water | q.s. |
| To make the whole | 100 |

By using the ingredients in the above-mentioned formulation, an ointment preparation is prepared by common method.

PREPARATION 8

| Ingredients | Amount (mg) |
| --- | --- |
| 1,1,3-Trimethyl-5-(2-fluoro-phenyl)biuret (Compound No. 7) | 100 |
| Lactose | 85 |
| Crystalline cellulose | 50 |
| Hydroxypropylstarch | 30 |
| Talc | 4 |
| Magnesium stearate | 1 |
| To make one tablet contains | 270 |

By using the ingredients in the above-mentioned formulation, tablet preparation is prepared by common method.

PREPARATION 9

| Ingredients | Amount (mg) |
| --- | --- |
| 1,1,3-Trimethyl-5-(2-trifluoro-methylphenyl)biuret (Compound No. 17) | 100 |
| Lactose | 50 |
| Potate starch | 50 |
| Crystalline cellulose | 109 |
| Magnesium stearate | 1 |
| To make one capsule contains | 310 |

By using the ingredients in the above-mentioned formulation, a capsule preparation is prepared by common method.

PREPARATION 10

| Ingredients | Amounts (mg) |
| --- | --- |
| 1,3,5-Trimethyl-1-phenylbiuret (Compound No. 53) | 200 |
| Lactose | 100 |
| Crystalline cellulose | 98 |
| Magnesium stearate | 2 |
| To make one capsule contains | 400 |

By using the ingredients in the above-mentioned formulation, a capsule preparation is prepared by common method.

PREPARATION 11

| Ingredients | Amounts (mg) |
| --- | --- |
| 1,3-Dimethyl-5-ethyl-1-phenylbiuret (compound No. 54) | 250 |
| Witepzol W-35 (A trade name for a suppository base material manufactured by and sold from Dynamite Nobel Company.) | 750 |
| To make one suppository contains | 1,000 |

By using the ingredients in the above-mentioned formulation, a suppository preparation is prepared by common method.

PREPARATION 12

| Ingredients | Amounts (mg) |
| --- | --- |
| 1,3-Dimethyl-5-n-propyl-1-phenylbiuret (Compound No. 55) | 100 |
| Sodium chloride | 16 |
| Distilled water for injection | q.s. |
| To make one ampule contains | 2 ml |

By using the ingredients in the above-mentioned formulation, an injection preparation (ampule) is prepared by common method.

PREPARATION 13

| Ingredients | Amount (g) |
| --- | --- |
| 1-Ethyl-3,5-dimethyl-1-(4-methoxyphenyl)biuret (Compound No. 61) | 2.0 |
| White vaseline | 23.0 |
| Stearyl alcohol | 22.0 |
| Propylene glycol | 12.0 |
| Sodium laurylsulfate | 1.5 |
| Ethyl p-oxybenzoete | 0.025 |
| Propyl p-oxybenzoete | 0.015 |
| Purified water | q.s. |
| To make the whole | 100 |

By using the ingredients in the above-mentioned formulation, an ointment preparation is prepared by common method.

What is claimed is:

1. A method of treating a patient requiring analgesia, said method comprising administering to said patient an analgesic amount of a compound of the formula (1):

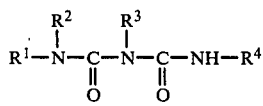

wherein $R^1$ is a lower alkyl group or a phenyl group; $R^2$ is a lower alkyl group, a phenyl group or a substituted phenyl group having chlorine atom(s), methyl group(s) or methoxy group(s) as the substituent(s), further $R^1$ and $R^2$ may form a single ring containing one or two hetero atoms including the adjacent nitrogen atom; $R^3$ is a hydrogen atom, a lower alkyl group or a phenyl group; $R^4$ is a phenyl group, a substituted phenyl group having halogen atom(s), trifluoromethyl group(s), methyl group(s), methoxy group(s), dimethylamino group(s), nitro group(s), hydroxyl group(s), acetyl group(s) or methylthio group(s) as the substituent(s), a benzyl group, a cyclohexyl group or a lower alkyl group; provided, however, that when $R^1$ is a lower alkyl group; $R^2$ is a lower alkyl group, a phenyl group, or a substituted phenyl group having chlorine atom(s) or methoxy group(s) as the substituent(s); or $R^1$ and $R^2$ form a single ring containing one or two hetero atoms including the adjacent nitrogen atom; and $R^3$ is a hydrogen atom, a lower alkyl group or a phenyl group; then $R^4$ is only a substituted phenyl group having hydroxyl group(s) as the substituent(s).

2. A method of treating a patient having a pyretic or inflammatory condition, said method comprising administering to said patient a therapeutically effective amount of a compound of the formula (1):

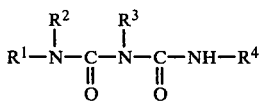

wherein $R^1$ is a lower alkyl group or a phenyl group; $R^2$ is a lower alkyl group, a phenyl group or a substituted phenyl group having chlorine atom(s), methyl group(s) or methoxy group(s) as the substituent(s), further $R^1$ and $R^2$ may form a single ring containing one or two hetero atoms including the adjacent nitrogen atom; $R^3$ is a hydrogen atom, a lower alkyl group or a phenyl group; $R^4$ is a phenyl group, a substituted phenyl group having halogen atom(s), trifluoromethyl group(s), methyl group(s), methoxy group(s), dimethylamino group(s), nitro group(s), hydroxyl group(s), acetyl group(s) or methylthio group(s) as the substituent(s), a benzyl group, a cyclohexyl group or a lower alkyl group.

3. Method of claim 1 or claim 2, wherein said amount is from about 10 to about 2000 mg per day for an adult.

4. Method of claim 1, or claim 2, wherein said daily dosage amount is divided into 2 or 3 portions which are separately administered.

5. Method of claim 1 or claim 2, wherein said compound of the formula (1) is administered orally or topically or by injection or suppository.

6. An analgesic, anti-inflammatory or anti-pyretic composition in the form of a tablet, capsule, granules, powder, injection preparation, suppository preparations topical ointment or cream or per oral syrup, elixir or oily suspension containing as the active ingredient an effective amount of 1,1,3,5-substituted biuret compound of the formula (1),

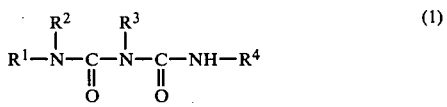

wherein $R^1$ is a lower alkyl group or a phenyl group; $R^2$ is lower alkyl group, a phenyl group or a substituted phenyl group having chlorine atom(s), methyl group(s) or methoxy group(s) as the substituent(s), further $R^1$ and $R^2$ may form a single ring containing one or two hetero atoms including the adjacent nitrogen atom; $R^3$ is a hydrogen atom, a lower alkyl group or a phenyl group; $R^4$ is a phenyl group, a substituted phenyl group having halogen atom(s), trifluoromethyl group(s), methyl group(s), methoxy group(s), dimethylamino group(s), nitro group(s), hydroxyl group(s) or methylthio group(s) as the substituent(s), a cyclohexyl group or a lower alkyl group; with a pharmaceutically acceptable carrier.

* * * * *